United States Patent [19]

Lee

[11] Patent Number: 4,874,520

[45] Date of Patent: Oct. 17, 1989

[54] CHROMATOGRAPHIC PROCESS

[75] Inventor: Siu-Leung Lee, Upper Arlington, Ohio

[73] Assignee: Battelle Development Corporation, Columbus, Ohio

[21] Appl. No.: 210,595

[22] Filed: Jun. 23, 1988

Related U.S. Application Data

[62] Division of Ser. No. 855,544, Apr. 23, 1986, abandoned.

[51] Int. Cl.[4] .............................................. B01D 15/08
[52] U.S. Cl. ..................................... 210/635; 210/656; 210/198.2:198.3; 502/401; 530/413; 530/417
[58] Field of Search ................. 502/62, 162, 170, 401, 502/404; 210/635, 656, 198.2, 198.3, 502.1; 530/413, 417

[56] References Cited

U.S. PATENT DOCUMENTS

| | | | |
|---|---|---|---|
| 3,440,864 | 4/1969 | Blume | 210/656 |
| 3,583,230 | 6/1971 | Patterson | 210/198.2 |
| 3,682,315 | 8/1972 | Haller | 210/198.2 |
| 4,070,285 | 1/1978 | Abrahams | 210/198.2 |
| 4,093,550 | 6/1978 | Stahl | 210/198.2 |
| 4,116,837 | 9/1978 | Biermacher | 210/198.2 |
| 4,280,905 | 7/1981 | Gunkel | 210/198.2 |
| 4,330,440 | 5/1982 | Ayers | 210/635 |
| 4,399,032 | 8/1983 | Mott | 210/198.2 |
| 4,422,975 | 12/1983 | Mitchell | 502/401 |
| 4,426,318 | 1/1984 | Fries | 502/402 |
| 4,565,632 | 1/1986 | Hatch | 210/656 |
| 4,587,232 | 5/1986 | Kawamura | 502/439 |

FOREIGN PATENT DOCUMENTS

| | | | |
|---|---|---|---|
| 56-92183 | 7/1981 | Japan | 210/198.2 |
| 59-1429 | 1/1984 | Japan | 210/198.2 |

OTHER PUBLICATIONS

Stephen L. Rosen, Fundamental Principles of Polymeric Materials, Wiley Interscience, Jun. 1982, p. 307.

Primary Examiner—Ernest G. Therkorn
Attorney, Agent, or Firm—Klaus H. Wiesmann; Benjamin Mieliulis

[57] ABSTRACT

A new class of chromatographic columns for reverse phase and ion exchange chromatography based on organotitanate coupling is disclosed along with separation processes using such media. The disclosed organo-titanate coupled matrices useful for reverse phase or ionic chromatographic separation can be made using titanate coupling agents in complete replacement of conventional silanating agents.

2 Claims, 3 Drawing Sheets

CHROMATOGRAPHIC PROCESS

This is a divisional of co-pending application(s) Ser. No. 06/855,544 filed on Apr. 23, 1986, now abandoned.

BACKGROUND OF THE INVENTION

This invention relates to separation technology particularly technology for accomplishing chemical separations including separations of biological materials. More particularly, this invention discloses organo-titanate coupled substrates for forming enhanced chromatographic columns or cartridges, including thin layer chromatography (tlc) plates and discloses a process for using coupled substrates for reverse phase and ionic batch separations.

The use of silanized support materials especially silanized siliceous support materials in chromatography is well established. Various hydroxy bearing inorganic materials are known as support materials including silicates, metal oxides including titanium oxides, clay, bentonite, and glass.

Chromatographic separation can be based on the difference in rate of migration of different components through a column. Separation is effected by partition of the components between the stationary phase and the mobile phase. Because of the different affinity of components towards the stationary phase, they are eluted at different rates.

In reverse phase chromatography the stationary phase is made nonpolar or hydrophobic. The strongest sorption occurs from polar eluents. Reversed phases are most often prepared by reacting silica gel with chloroalkylsilanes or alkoxysilanes.

Ion exchange chromatography involves an insoluble matrix having covalently bonded dissociable functional groups at accessible sites. The functional groups typically are sulfonic or carboxyl for cation exchanges and tertiary amino or quaternary ammonium groups for anion exchanges. Separation is based on the affinity differences of ions toward their counter-ions in the ion exchange matrix and those dissolved in the eluent.

Chemical modification of chromatographic substrate materials to produce chemically modified support materials has involved use of silane coupling agents. Use of these materials involves considerable expense. Effective alternative materials, particularly more available and economic materials would be advantageous and of commercial significance.

Particularly in the case of large scale separations of biological materials, batch processing has not been practical due to the prohibitive cost factors in using large quantities of silanes. The process according to this invention makes batch scale separations of biological materials commercially possible by disclosing use of the inexpensive organotitanates in separations in complete replacement of silanes.

DESCRIPTION OF RELATED ART

Various hydroxy-bearing materials have been used as packing materials for chromatographic columns including carbon black, aluminas, and most often silicas and silica gels.

Silica gel is the most frequently used adsorbent as it can be prepared in high purity and with various physical properties including specific surface area, pore volume, and pore size. It is inexpensive and its rigidity makes it useful in column chromatography and thin layer chromatographic plates.

By chemically bonding compounds to the silica gel, chemically modified chromatographic packing materials have been devised. Typically this involves bonding organic compounds, particularly chloro or alkoxysilanes forming new Si-O-Si bonds. Di- or tri- halo silanes or the corresponding alkoxysilanes are typically employed.

Chemically modified silica gel columns possess advantages over conventional particles coated with liquid phase. These advantages can include:

(a) eluent need not be saturated with the liquid phase,
(b) elimination of precolumn,
(c) in sample isolation from the eluent there is no contamination from the stationary phase,
(d) the stationary phase cannot be stripped off thus overcoming problems of mechanical erosion at high flow rates,
(e) various programming techniques such as gradient elution can be employed,
(f) column equilibrium is less subject to disruption by external effects such as temperature or eluent moisture.

By appropriate selection of functional groups it has been known to use chloro or alkoxysilanes to form other chemically bonded stationary phases for specific applications. Stepwise preparations or derivatives are possible with reversed phase, cation exchangers with alkyl or arylsulfonic acid groups, and anion exchangers with amino, dialkylamino or quaternary ammonium groups.

While many silanizing agents are known for forming chemically modified packing materials, yet these silanes typically involve considerable expense. An alternative material, particularly a more cost-effective alternative to silylating agents would be an advance in the art. Chemical modifiers for packing materials, until this invention, were almost exclusively restricted to silanes.

Use of titanium coupling agents for filler applications in polymers and composites is disclosed in patents such as 4,141,751; 4,163,004 and 4,308,298.

Titanium dioxide has long been recognized as a support material for chromatographic applications.

No where in the art until this invention; however, has there been a disclosure that effective chromatographic supports or matrices for reverse phase or ionic chromatographic separations can be made using titanate coupling agents in complete replacement of silanizing agents.

It is an object of the present invention to disclose an alternative to silanizing agents and particularly, a novel class of solid supports for reverse phase and ionic chromatography making possible a new line of chromatographic columns.

It is an object of the present invention to disclose an alternative to silanizing agents thus making feasible new batch separation processes based on functional but relatively inexpensive separation media for reverse phase and ion exchange chromatography and related processes employing chemically modified chromatographic substrates

SUMMARY OF THE INVENTION

This invention discloses a new class of chromatographic columns and thin layer chromatography plates based on organotitanate coupled hydroxy bearing solid supports or packing materials useful in reverse phase or ion exchange chromatography. The invention discloses essentially a new process for reverse phase or ion exchange chromatographic separations of chemicals by means of organotitanate coupled solid support materials in complete or partial replacement of silanized, chemically modified solid support materials. The term "chemicals" is understood to include organic chemicals and also biological chemicals such as enzymes, coenzymes, prosto-glandins, steroids, lipids, amino acids, and other such chemicals involved in or derived from life processes, all by way of illustration and not limitation.

More particularly, the invention discloses a new chromatographic column for reverse phase or ionic chromatographic separation of chemicals from a mixture comprising:

a cartridge having an internal chamber and having entrance and exit orifices, a solid support material within said chamber consisting of a porous hydroxy bearing material, an organotitanate having hydrophobic functionality or an ionizable moiety and chemically coupled to said solid support material by a condensation reaction with the hydroxy groups, coupling means at said entrance and exit orifices for installing the cartridge in the flow path of a fluid mixture.

As is readily evident, the solid support material absent the cartridge can be fashioned into a new thin layer chromatography plate.

The invention also discloses an improved process for separating chemical substances based on their hydrophobic or ionizable moieties. Separations accomplished by ion exchange or reverse phase chromatography of the type using a stationary phase consisting of a chemically modified support material capable of reversibly fixing macromolecules wherein the improvement comprises:

providing a hydroxy bearing support material, reacting the support material with an organotitanate that is a hexavalent coordinate compound or an organotitanate of the formula, $$R_n-Ti-R'_{4-n}$$

wherein Ti is tetravalent, wherein $R_n$ is a hydrolyzable group linked to titanium through oxygen and is selected from the group consisting of alkoxy, and (Note: n is defined as 2 for purposes of this application when $R_n$ is a cyclical group)

wherein R' is a hydrophobic organofunctional group and is selected from the group consisting of alkoxy, aryloxy, alkylester, acrylate, methacrylate, amino aromatic sulfonyl, alkyl aromatic sulfonyl, pyrophosphate, and alkyl phosphato, then contacting the organotitanate reacted support material with a solution mixture of chemical substances one constituent of which has ionizable or hydrophobic functionality so as to reversibly fix the chemical substance to the organotitanate reacted support material, and eluting the fixed chemical substance with an ion containing solution or hydrophobic solvent.

DETAILED DESCRIPTION

FIGS. 1, 2, 3 and 4 show several designs for chromatographic columns according to this invention wherein the packing material is a hydroxy bearing material coupled by a condensation reaction with an organotitanate to yield a new class of chromatographic columns or cartridges useful for reverse phase or ionic separations.

Chromatographic columns typically are constructed of a tube or cartridge 1 filled with packing material and attached, connected or coupled to an apparatus, process vessel, or most often an instrument by means of various fittings or coupling means 4. The trend in the art is away from fixed cartridges and to the use of replaceable cartridges insertable into a holder to form the column. The replaceable cartridge is typically a tube having solid substrate or sorbent within it. The cartridge conventionally is fitted with an end cap 4A and bed support. The cartridge fits inside the holder tube 2 which has end fittings that compress the caps on the cartridge forming a leak proof seal. Connections to the fluid flow path of an instrument, production apparatus or other vessel, are made directly to the holder tube. Replacing of packing materials in chromatographic columns is simplified by the insertable cartridge concept.

Figure 1:
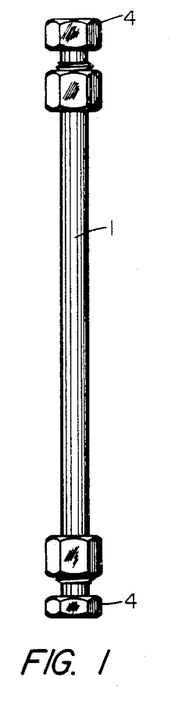
FIG. 1 is a view of a chromatographic column.

For clarity and for purposes of this invention the term chromatographic cartridge is intended to encompass both columns that are fixed tubes loaded with organotitanate coupled packing material as in FIG. 1 and also designs using the newer replaceable cartridges or other minor variations.

In FIG. 1 the chromatograph column is depicted as a fixed cartridge 1 into which is packed organotitanate coupled silica or the hydroxy bearing material.

Figure 2:
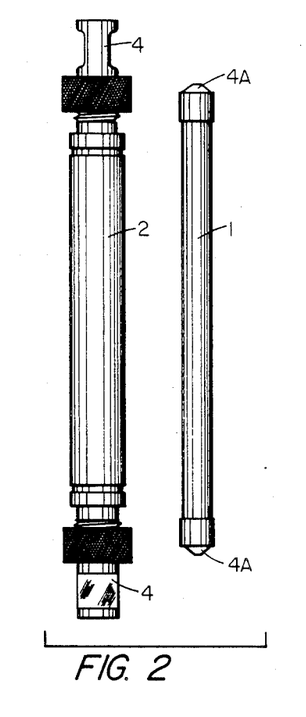
FIG. 2 is a view of a chromatographic column wherein the packing material is in an insertable cartridge.
Figure 3:
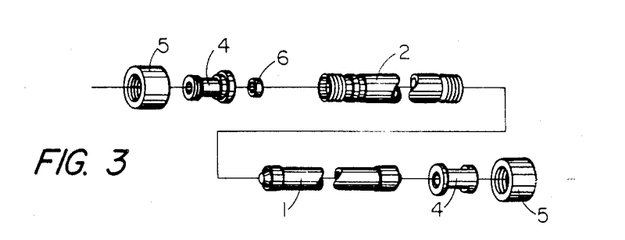
FIG. 3 is an explode view of the chromatographic column and cartridge of FIG. 2.

FIG. 3 is an exploded view of a typical column using the cartridge concept as in FIG. 2. Organotitanate coupled silica or other hydroxy bearing filler can be compressed into cartridge 1 which then fits into holder 2. Indicated also is prefilter 6, fittings or coupling means 4 and retaining or compressing rings 5.

Figure 4:
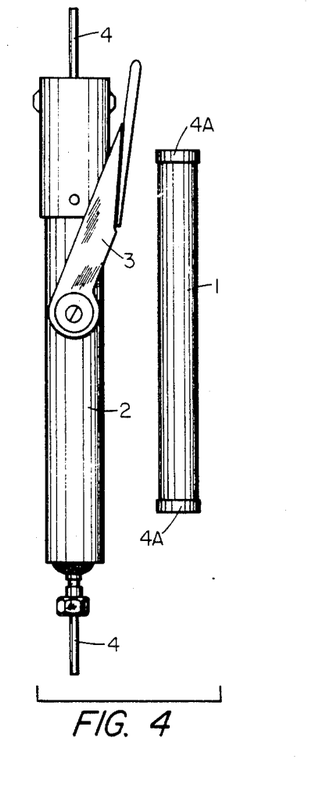
FIG. 4 is an alternate design for a chromatographic column also using an insertable cartridge.

FIG. 4 depicts another chromatographic column also using an insertable cartridge 1 wherein holder 2 is a two part assembly, compressed and held together or released by either depressing or lifting of lever 3.

This invention discloses a novel class of chromatographic columns based on titanium coupled chromatographic media. The chromatographic material of this invention is a hydroxy bearing substrate material coupled with an organotitanate coupling agent by means of reaction with the surface hydroxyl groups yielding a hydrophobic or ion exchange substrate. The organofunctional group can be selected to be useful in reverse phase or ionic chromatography by appropriate selection of functional groups.

The titanium coupling agent coupled to the solid support material can be characterized by the formula $$R_n—Ti—R'_{4-n}$$

wherein n is 1, 2, or 3, preferably 3; R' is a hydrophobic or ionizable organofunctional group attached to titanium through oxygen, and R is a hydrolyzable group such as an alkoxy group converted to an alcohol group on hydrolysis.

Preferably the titanium coupling agent is of the formula R Ti R'$_3$, wherein R and R' are as above defined. The hydrolyzable groups usually are alkoxy. If more than one alkoxy group is a substituent it is evident they need not be the same though such is preferred.

R is a hydrolyzable group linked to titanium through an oxygen and can be selected for example from the group consisting of alkoxy, oxyacetate chelate and A,B ethylene chelate Preferably R is isopropoxy.

R' is organofunctional group having a hydrophobic or ionizable moiety and is linked to titanium through an oxygen. R' is selected based on the desired character of the final chromatographic media whether for reverse phase application or ion exchange. For example, R' can be dioctylphosphato, tri (dioctylphosphato), or isostearoyl for reverse phase chromatography. R' can be an alkyl- or aryl-amino group for anion exchange. R' can be a carbonphosphate group for cation exchange or for hydrophobic i.e., reverse phase interactions.

The hydroxy bearing inorganic or organic substrate materials i.e., X-OH can include various silicas, glass, sand, clay, fiberglass, silica gel, or celluloses or carbohydrates such as dextrans, agarose, or metal oxides. Selection of the substrate is based on the abundance of hydroxy groups.

The resulting coupled materials have been found useful in chromatographic techniques specifically ion exchange chromatography and reversed phase chromatography thus enabling the construction of new types of chromatographic columns and cartridges. The suitability for particular chromatographic techniques would be dependent on the nature of the organofunctional group attached to titanium, for example, (wherein x is a substrate such as silica):

| | Application |
|---|---|
| $X—O—Ti(—O—\overset{O}{\overset{\|}{C}}—C_{17}H_{35})_3$ | reversed phase |
| $X—O—Ti(—O—C_6H_4—C(CH_3)_2—C_6H_5)_3$ | reversed phase |
| $X—O—Ti(—O—\overset{O}{\overset{\|}{P}}(OH)—O—\overset{O}{\overset{\|}{P}}(OC_4H_9)(OCH_3))_3$ | cation exchange hydrophobic interaction |
| $X—O—Ti(+O—CH_2CH_2—NH—CH_2CH_2—NH_2)_3$ | anion exchange |

Since titanates bearing various organofunctional groups can be selected, these coupling agents allow selectivity in forming chemically modified chromatographic substrates. For example, the following organotitanates can be coupled to hydroxy bearing substrates to yield chromatographic media useful for the following applications:

| Name | Formula Type $R_n—Ti—R^2_{4-n}$ | Application |
|---|---|---|
| isopropyl tri(dioctylphosphato) titanate | $CH_3—CH(CH_3)—O—Ti(—O—P(=O)(O—C_8H_{17})_2)_3$ | Reverse phase |
| isopropyl tri(N—ethylamino-ethylamino) titanate | $CH_3—CH(CH_3)—O—Ti[+O—C_2H_4—NH—C_2H_4—NH_2]_3$ | Anion Exchange |
| di(butyl, methyl pyrophosphato)ethylene titanate plus di(dioctyl, hydrogen phosphite) for storage stability | $(CH_2—O)_2Ti[—O—P(=O)(OH)—O—P(=O)(O—C_4H_9)(O—CH_3)]_2$ | Weak cation exchange |

-continued

| Name | Formula Type | Application |
|---|---|---|
| isopropyl triisostearoyl titanate | $CH_3-CH(CH_3)-O-Ti-(-O-CO-C_{17}H_{35})_3$ | Reverse phase |
| isopropyl tri-(dioctylpyrophosphato) titanate | $CH_3-CH(CH_3)-O-Ti-(-O-P(O)(OH)-O-P(O)(OC_8H_{17})_2)_3$ | Reverse phase |
| isopropyl tricumylphenyl titanate | $CH_3-CH(CH_3)-O-Ti-(-O-C_6H_4-C(CH_3)_2-C_6H_5)_3$ | Reverse phase |

Useful titanate coupling agents for forming chromatographic media include monoalkoxy titanate coupling agents such as:

reverse phase isopropyl triisostearoyl titanate isopropyl methacryl diisostearoyl titanate isopropyl dimethacryl isiostearoyl titanate ion exchange isopropyl tridodecylbenzene-sulfonyl titanate reverse phase isopropyl diacryl isostearoyl titanate ion exchange isopropyl tri(dioctylphosphato) titanate

-continued reverse phase
isopropyl 4-aminobenzene-sulfonyl di(dodecylbenzene-sulfonyl) titanate reverse phase
isopropyl trimethacryl titanate isopropyl tricumylphenyl titanate isopropyl di(4-amino-benzoyl) isostearoyl titanate ion exchange
reverse phase
isopropyl tri(dioctylpyro-phosphato) titanate reverse phase
isopropyl triacryl titanate ion exchange
isopropyl tri(N ethylamino-ethylamino), titanate isopropyl tri(2-aminobenzoyl) titanate isopropyl tri(butyl, octyl pyrophosphato) titanate

| | |
|---|---|
| di(butyl, methyl pyrophosphato) isopropyl titanate |  |

Also useful are oxyacetate chelate titanate coupling agents such as:

-continued reverse phase

| | |
|---|---|
| titanium isostearate methacrylate oxyacetate |  |
| titanium acrylate isostearate oxyacetate |  |
| titanium dimethacrylate oxyacetate |  |
| titanium di(cumylphenylate) oxyacetate |  |
| titanium diacrylate oxyacetate |  | ion exchange

| | |
|---|---|
| titanium di(dioctylpyrophosphate) oxyacetate |  |
| titanium di(butyl, octyl pyrophosphate) oxyacetate |  |

Also useful are A B ethylene chelate titanate coupling agents such as:

| | |
|---|---|
| diisostearoyl ethylene titanate |  | reverse phase

| | |
|---|---|
| di(dioctylphosphato) ethylene titanate |  |
| 4-aminobenzene sulfonyl dodecylbenzene sulfonyl ethylene titanate |  |
| ion exchange di(dioctylpyrophosphato) ethylene titanate |  |
| di(butyl, methyl pyrophosphato) ethylene titanate |  |

Coordinate titanate coupling agents such as the following are also useful for forming chemically modified chromatographic substrates:

reverse phase

| | |
|---|---|
| tetraisopropyl di(dioctylphosphito) titanate |  |
| tetraoctyloxytitanium di(ditridecylphosphite) |  |
| tetra(2,diallyoxymethyl-1-butoxy-titanium di-(di-tridecyl) phosphite |  |

The organotitanate coupled chromatographic media of the present invention offers many advantages over conventional chemically modified packing materials. The organotitate coupling agents often can be coupled in a single step and without generation of HCl gas as is involved in use of chlorinated silanes. Coupling to the hydroxy bearing surface is typically accomplished by the simple step of coating the surface with the organotitanate.

The organotitanate can be dissolved in a solvent prior to contacting to the hydroxy bearing surface to effect coupling. Coupling can be enhanced through mild heating, though simple immersion of the hydroxy bearing substrate in the organotitanate at ambient temperature was found suitable to effect coupling in most cases. It may be advantageous with some substrates to expose them to humid conditions prior to coupling to insure a maximum number of possible hydroxy groups available for coupling.

The organotitanate coupled substrate materials for use in forming novel columns, tlc plates and related chromatographic batch separations can be prepared by coating or contacting the hydroxy bearing substrate material with one of the enumerated organotitanates. Preferably a dilute organotitanate solution in a solvent such as toluene or other solvent such as isopropanol is employed. While covalent coupling to the hydroxybearing surface often can occur at room temperature, it was found advantageous to immerse the substrate in the organotitanate solution and heat to boiling for about 0.5 minute. The recovered treated substrate material can then be packed into a column or cartridge or applied to tlc plates. Forming the tlc plate is however best accomplished by immersing the entire tlc plate in the organotitanate solution to treat the finished plate.

Since organotitanates typically can be made less expensively than the silane counterparts they can replace, this invention makes large volume batch processes viable. Thus the invention encompasses not only new chromatographic columns but also a new process of reverse phase or ion exchange chromatography based on organotitanate coupled solid support materials.

The stationary phase or support material coupled with organotitanate, rather than being placed in a chromatographic column, can be directly added to a reactor vessel. In a typical process, for example a batch process, reverse phase or ionic separation can be accomplished en masse. Until this invention, economics attendant to use of silane couplers, made batch processing prohibitevely expensive. The invention discloses an economical and an improved process for separating chemical substances from a solution mixture by reverse phase or ion exchange chromatography of the type using a stationary phase consisting of a chemically modified support material capable of fixing reversibly macromolecules wherein the improvement comprises providing a hydroxy bearing support material such as silica, glass, metal oxide or cellulose preferably as a powder or particulate, then reacting the hydroxy bearing solid support material with any one of the organotitanates specified earlier herein.

The organotitanate coupled support material is contacted with a solution mixture of chemical substances, one constituent of which has hydrophobic or ionizable functionality, so as to cause reversible fixing of the target chemical substance to the organotitanate reacted support material.

The target chemical is then recovered with the solid support material. The fixed target chemical can be isolated from the other fluids in the reactor vessel. The target chemical can be recovered by elution or washing with an ionic solution such as Nacl in ionic exchange or with a hydrophobic solvent for reverse phase separations.

The invention is further illustrated by the following examples.

EXAMPLES

1. Titanate treated silica gel as anion exchanger.

Neoalkoxy tri(N-ethylamino-ethylamino) titanate was dissolved in isopropanol to yield a 1% solution (1 g in 100 ml). To 10 g of silica gel (Amicon, particle size 20–45 um 250A pore) 30 ml of the titanate solution was added. The suspension was heated to boiling for 5 minutes, cooled and filtered through a fritted-disc funnel and washed with isopropanol.

The treated silica gel was packed into a Bio Rad ® econocolumn (1 cm×1.5 cm). The treated gel was equilibrated with 10 MM potassium phosphate buffer at pH 6.8. One ml of rabbit serum was applied to the column and eluted with the same buffer. The obtained fractions were monitored using a Spectromonitor ® III (LDC) at 280 mm and collected. Two major fractions were obtained. Purity of the fractions was assessed by SDS gel electrophoresis against a known standard. 15 bands were visible in Fraction 1 while only 6 were visible in Fraction 2 with greater than 95% of the protein in the albumin band.

The loading capacity of the titanate treated silica gel appears high, accommodating 1 ml of pure serum onto 2.5 ml of packing.

The treated silica gel particle size 20–45 um of the previous example was formed into a slurry in 10 mM potassium phosphate pH 6.8 and packed into a 4.6 mm×25 cm stainless steel column.

This column was used for separation of the following protein mixtures:
(1) E. coli protein mixture (induced for λ repressor)
(2) milk proteins
(3) Bio Rad ® protein standards (cytochrome C, myoglobin, ovalbumin, albumin, γ-globulin).

The titanate treated silica gel allowed separation of the protein mixtures with moderately high resolution. Little observable back pressure was noted. By changing the particle size of the silica gel from 20–45 um to 5 or 10 um, the resolution can be enhanced to be comparable to commercial HPLC grade anion exchangers.

Example 2

Commercial silica gel thin layer chromatography plates were dipped in 2% isopropyl triisostearoyl titanate in toluene for 5 minutes and air dried. The plates were then washed for 5 minutes in toluene to remove any unreacted isopropyl triisostearoyl titanate. The treated silica gel was referred to as "T-SIL". Felt tip pen inks were spotted on each plate and the inks were separated using mixture of acetonitrile and water as a developing solvent.

Table 1 shows the separation of some inks on T-SIL TLC plates as compared to commercial normal phase and reverse phase TLC plates. Red ink and green ink for felt tip pens contain polar components, which did not migrate on normal phase silica gel in a solvent system containing chloroform/methanol (9:1). On commercial reverse phase TLC plates, the red ink and green ink components were each separated into two components respectively, using a solvent system containing acetonitrile/water (5:5). The separation of dye components on the isopropyl triisostearoyl titanate treated silica gel plate was similar to that on commercial reverse phase TLC plates, except that the solvent system used was acetonitrile/water (2:8), with much lower consumption of the more expensive organic solvent component.

The commercial reverse phase and the commercial normal phase TLC plates when subject to the high-water solvent system disintegrated. The entire gel surface was cracked. Disintegration of the gel occurred with the commercial reverse phase TLC plate in a solvent system containing less than 50% organic solvents.

The experiment clearly demonstrates the change of normal phase behavior to reverse phase behavior after the silica gel plate was modified by isopropyl triisostearoyl titanate. It also shows that the modified silica gel can be run in a solvent system with high water content to achieve the same separation results. By so doing, the user saves on lower consumption of expensive organic solvent.

TABLE 1

Thin Layer Chromatography of Inks on Treated Silica Gel

| Media | Ink Components (Rf) | | |
|---|---|---|---|
| | Red | Green | Purple |
| COMMERCIAL NORMAL PHASE TLC | 0.0 | 0.00 | 0.95 |
| chloroform/methanol 9:1 | 0.15 | | |
| COMMERCIAL REVERSE PHASE TLC | 0.57 | 0.60 | 0.00 |
| acetonitrile/water 5:5 | 0.61 | 0.65 | |
| NOVEL T-SIL, REVERSE PHASE TLC | 0.70 | 0.70 | 0.00 |
| acetonitrile/water 2:8 | 0.77 | 0.79 | |

Example 3—Ion Exchange

Isopropyl tri(N-aminoethyl-aminoethyl) titanate, was an organotitanate bearing both primary and secondary amines, coupled to silica gel and demonstrated as an anion exchanger.

Silica gel (20–45 um, 250 A) was reacted with 1% solution (organotitanate/silica gel) of isopropyl tri(N-aminoethyl-aminoethyl) titanate in isopropanol for 1 hr. The excess organotitanate was removed by washing with isopropanol. The modified silica gel was packed into a column, 1 cm×4.5 cm. Protein separation was accomplished with this column by eluting with sodium phosphate buffer at 10 mM, pH 6.8, at a flow rate of 1 ml/min. Protein eluates were monitored spectrophotmetrically at 280 nm. One ml of undiluted rabbit serum sample was separated into two major bands. SDS gel electrophoresis showed that the second contained serum albumin at greater than 90% purity.

Figure 5:
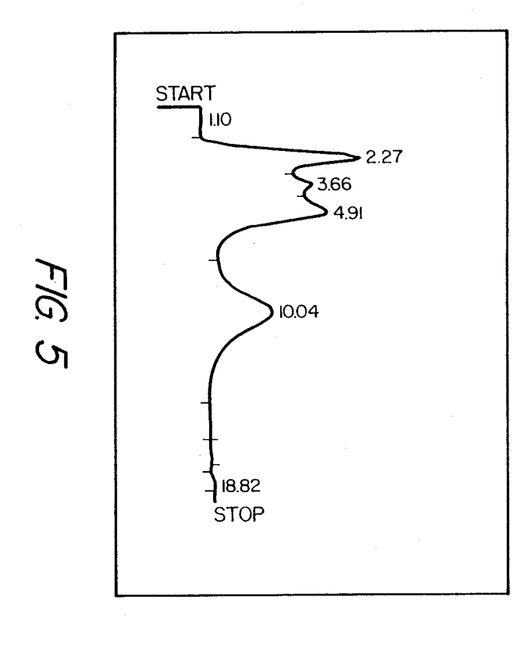
FIGS. 5, 6, and 7 are graphical printouts of chromatographic separations of mixtures using organo-titanate-treated chromatographic media of the invention.

Another column 4.6 mm×25 cm was packed with the same isopropyl tri(N-aminoethyl-aminoethyl) titanate modified material. A mixture of thyroglobulin, gamma globulin, ovalbumin, myoglobin and vitamine B12 was applied to the column. Four major bands were resolved as shown in FIG. 5.

Figure 6:
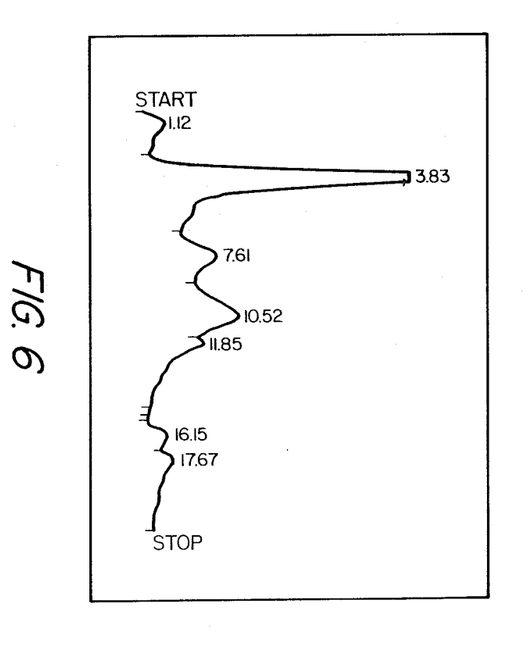

An E. coli crude protein extract was separated into at least seven bands by the isopropyl tri(N-aminoethyl-aminoethyl) titanate ion exchange column (FIG. 6).

Example 4

Silica gel (20-45 um, 250 A) was modified by refluxing with 1% isopropyl triisostearoyl titanate in toluene for 1 hour. The excess organotitanate was removed by washing with toluene.

An aqueous solution of 2,4,5-trichlorophenoxyacetic acid (2,4,5-T, in the free acid form) was prepared by dissolving 0.8 mg of the compound in 5 ml water. The aqueous solution of 2,4,5-T was mixed vigorously with the modified silica gel for 2 minutes. Then the solid was separated from the solution by centrifugation. Unadsorbed 2,4,5-T was assayed by absorbance at 286 nm. A decrease in absorbance at 286 nm indicates decreased concentration of 2,4,5-T in the solution. The decrease in concentration of 2,4,5-T in the treated solution was proportional to the amount of modified silica gel added ranging from 50 to 400 mg. Over 80% of the 2,4,5-T was adsorbed by the modified silica gel. A parallel experiment with unmodified silica gel showed that no adsorption took place. There was even an apparent increase in 2,4,5-T concentration due to adsorption of water by the plain silica gel. The materials adsorbed to the treated silica gel may be eluted from the solid support by a non-polar organic solvent.

Example 5—Reverse Phase Liquid Chromatography

Fifty grams of silica gel (20-45 um or 10 um, 250 A) was heated in 200 ml of 0.1M HCl at 90 C in a sealed bottle for at least 24 hr to maximize the exposure of silanol groups. The silica gel was filtered through fritted disc funnel and washed till neutral. The acid—treated silica gel was then dried at 150 C for at least 8-12 hours to remove traces of water. The dry silica gel was refluxed with 2% isopropyl triisostearoyl titanate in dry toluene for 18 hours. The treated silica gel was washed with toluene and dried. In end-capped packings, the silica gel was further reacted with a 2% chlorotrimethylsilane in toluene for 30 minutes. The material was then washed with toluene and dried. The treated silica gel was slurried in acetonitrile and packed into a column 4.6 mm ×25 cm using an Altex pump with a reservoir packer.

p-Nitrobenzaldehyde, m-nitroacetanilide, p-nitroanisole were used as model compounds to evaluate the performance of a column packed with 10 um isopropyl trisostearoyl titanate modified silica gel (T-SIL). Separation of the three compounds was achieved best at 5% acetonitrile in water as the solvent system at 1 ml/min. An increase in acetonitrile to 10% or an increase of the flow rate to 2 ml/min reduced the k' and alpha value (k' =relative migration of the solute compared to the solvent front; alpha value=relative migration of two solutes).

Figure 7:
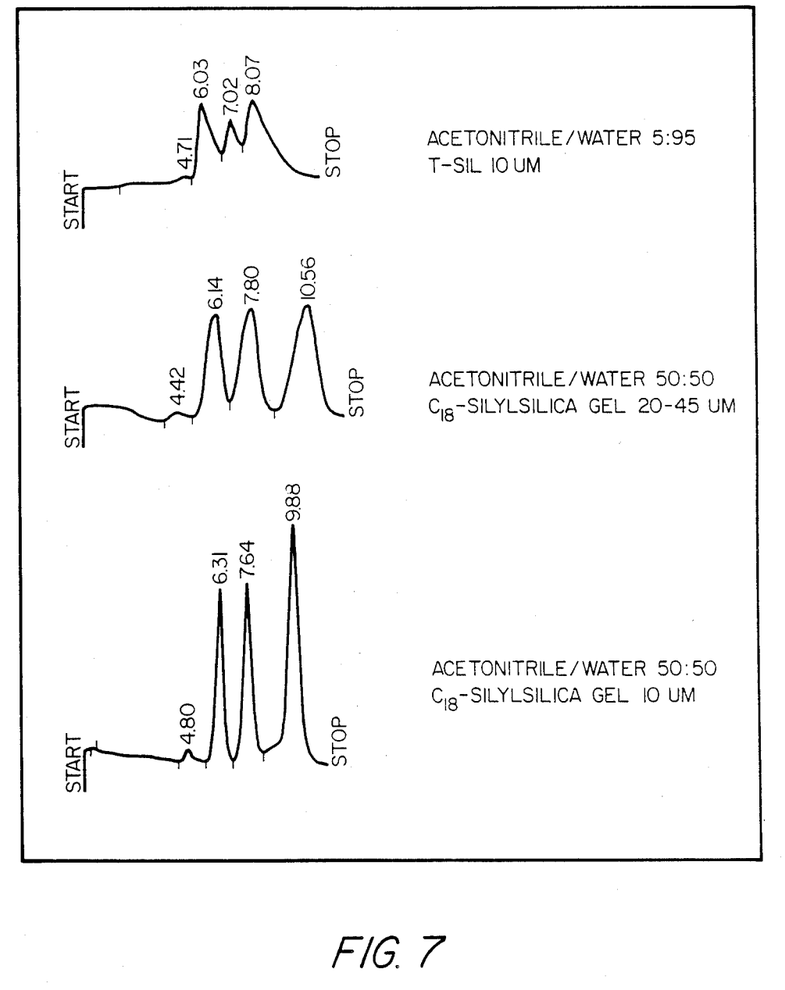

The separation was compared with a column packed with commercial reverse phase silica gel (20-45 um, Amicon) and a commercial C18-silica gel column (Radialpak, 10 um). Using a solvent system of 5% acetonitrile in water, separation of the model compounds on the T-SIL column was similar to that on C18-silylated reverse phase columns. It can be observed that the separation of the nitrocompounds on the commercial reverse-phase column (Radialpak) is similar to that obtained on the T-SIL column except that a much lower organic solvent ratio is required for the T-SIL (20% acetonitrile versus 50% as in the commercial reverse-phase packing). The resolution on T-SIL (particle diameter=10 u) is better than the radialpak (particle diameter=20-45 u) (FIG. 7).

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

I claim:

1. An improved process for separating ionizable chemical substances from a solution mixture by ion exchange chromatography of the type using a stationary phase consisting of a chemically modified support material capable of reversibly fixing macromolecules wherein the improvement comprises:

providing a hydroxy bearing support material, reacting the support material with an organotitanate of the formula, wherein n is 1, 2, or 3, wherein $R_n$ is a hydrolyzable group linked to titanium through oxygen and is selected from the group consisting of alkoxy, wherein R' is a hydrophobic organofunctional group linked to titanium through oxygen and is each independently selected from alkoxy, arylalkoxy, alkyl ester, acrylate, methacrylate, alkenylester, alkyl phosphato, alkyl pyrophosphato, aminoalkoxy, aminoalkylarylester and quaternary ammonium salt, contacting the organotitanate reacted support material with a solution mixture of chemical substances one constituent of which has an ionizable functionality so as to reversibly fix the chemical substance with ionizable functionality to the organotitanate reacted support material, eluting the fixed ionizable chemical substance with an ionic solution.

2. An improved process for separating ionizable chemical substances from a solution mixture by ion exchange chromatography of the type using a stationary phase consisting of a chemically modified support material capable of reversibly fixing macromolecules wherein the improvement comprises:

providing a hydroxy bearing support material, reacting the support material with an organotitanate of the formula, wherein R is a hydrolyzable group linked to titanium through oxygen and is independently selected from alkoxy and allyloxyalkoxy, wherein R' is an ionizable organofunctional group and is an alkyl phosphite, contacting the organotitanate reacted support material with a solution mixture of chemical substances one constituent of which has an ionizable functionality so as to reversibly fix the chemical substance with ionizable functionality to the organotitanate reacted support material, eluting the fixed ionizable chemical substance with an ionic solution.

* * * * *